United States Patent
Barnum et al.

(10) Patent No.: US 9,108,911 B1
(45) Date of Patent: Aug. 18, 2015

(54) PROCESS FOR THE MANUFACTURE OF DI-TMP

(71) Applicant: Oxea Bishop LLC, Dallas, TX (US)

(72) Inventors: A. Rider Barnum, Bay City, TX (US); Christopher John Bischoff, Bay City, TX (US)

(73) Assignee: OXEA BISHOP LLC, Dallas, TX (US)

( * ) Notice: Subject to any disclaimer, the term of this patent is extended or adjusted under 35 U.S.C. 154(b) by 0 days.

(21) Appl. No.: 14/540,620

(22) Filed: Nov. 13, 2014

Related U.S. Application Data

(60) Provisional application No. 61/970,599, filed on Mar. 26, 2014.

(51) Int. Cl.
*C07C 41/16* (2006.01)
*C07C 41/01* (2006.01)

(52) U.S. Cl.
CPC .................. *C07C 41/16* (2013.01); *C07C 41/01* (2013.01)

(58) Field of Classification Search
None
See application file for complete search history.

(56) References Cited

U.S. PATENT DOCUMENTS

| | | | |
|---|---|---|---|
| 3,740,322 A | 6/1973 | Wada et al. | |
| 3,962,347 A | 6/1976 | Herz | |
| 5,324,863 A * | 6/1994 | Sjogreen et al. | 568/680 |
| 5,840,994 A | 11/1998 | Ninomiya et al. | |
| 6,515,152 B1 | 2/2003 | Annby et al. | |
| 2004/0254405 A1 | 12/2004 | Kuzuhara et al. | |
| 2012/0010435 A1 | 1/2012 | Rauchschwalbe et al. | |
| 2013/0131391 A1 | 5/2013 | Kreickmann et al. | |

FOREIGN PATENT DOCUMENTS

| | | | | |
|---|---|---|---|---|
| GB | 787406 A | | 12/1957 | |
| JP | 107669 A | | 1/1998 | |
| JP | 2003335716 A | * | 11/2003 | ............. C07C 41/09 |
| JP | 2003335717 A | | 11/2003 | |
| WO | 9205134 A1 | | 4/1992 | |
| WO | 0114300 A1 | | 3/2001 | |
| WO | 2013072006 A1 | | 5/2013 | |
| WO | 2013072007 A1 | | 5/2013 | |
| WO | 2013072008 A1 | | 5/2013 | |
| WO | 2014024717 A1 | | 2/2014 | |

OTHER PUBLICATIONS

Machine translation of the Description section of JP 2003335716A (performed on Apr. 12, 2015 at http://worldwide.espacenet.com).*
Pattison, D.B., "Cyclic Ethers Made by Pyrolysis of Carbonate Esters", J. Am. Chem. Soc., Jul. 5, 1957, 3455-3456, vol. 79, 13.
Tan, Qiaohua et al. "Electrochemical Behaviors and Anion Recognition of Ferrocene Modified Hyperbranched Polyether." Macromolecules, 2009, 4500-4510, 42(13), American Chemical Society, Washington, D.C., USA.

* cited by examiner

*Primary Examiner* — Brian J Davis
(74) *Attorney, Agent, or Firm* — Michael W. Ferrell

(57) ABSTRACT

A method of making di-TMP includes reacting TMP and a dialkyl carbonate in the presence of a base catalyst in a reaction medium to form an oxetane of TMP in the reaction medium; providing additional TMP and an acid catalyst to the reaction mixture and reacting the oxetane in situ with the additional TMP to produce di-TMP; and recovering di-TMP. The process may be carried out in sequential reaction zones by feeding the reaction medium forward or carried out sequentially in a single reactor. Preferably, one or all of the following conditions are met: (i) said acid catalyst is a strong acid catalyst or (ii) said base catalyst is a strong base catalyst; or (iii) the molar ratio of TMP/dialkyl carbonate employed in the method is greater than 2.5.

23 Claims, 2 Drawing Sheets

PROCESS FOR THE MANUFACTURE OF DI-TMP

CLAIM FOR PRIORITY

This application is based on U.S. Provisional Application No. 61/970,599 filed Mar. 26, 2014 of the same title, the priority of which is hereby claimed and the disclosure of which is incorporated herein by reference.

TECHNICAL FIELD

The invention relates to a process for the manufacture of di-TMP from trimethylolpropane (TMP) by reaction with a dialkyl carbonate. In a first stage, TMP is reacted with the dialkyl carbonate with a base catalyst to form an oxetane of trimethylolpropane in the reaction mixture; the oxetane in the reaction mixture medium is then reacted in situ with an acid catalyst and additional trimethylolpropane to form di-TMP.

BACKGROUND di-TMP of the formula $[C_2H_5C(CH_2OH)_2-CH_2-]_2\text{-}0$, having the structure:

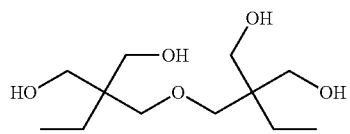 [SMILES: CCC(CO)(CO)COCC(CC)(CO)CO]

may also be referred to as 2-[2,2-bis(hydroxymethyl)bu-toxymethyl]-2-ethylpropane-1,3-diol. This material is of industrial significance as a valuable starting material for the production of alkyd resins, plasticizers and lubricants. di-TMP is found in high-boiling fractions and residues of the distillative work-up of the trimethylolpropane preparation. The prior art discloses processes for obtaining di-TMP from these residues.

According to DE 2058518 A1 (counterpart to U.S. Pat. No. 3,740,322 to Wada et al.), the di-TMP containing distillation residue is subjected to a steam distillation with superheated steam under reduced pressure. After removal of water, di-TMP is obtained from the resulting aqueous distillate, and can be recrystallized if required from an organic solvent, for example acetone.

DE 2358297 A1 (counterpart to U.S. Pat. No. 3,962,347 to Herz), discloses the simple crystallization of an aqueous solution of the distillation residue, wherein the salt concentration in the aqueous solution is adjusted to a particular ratio in order to enable the precipitation of di-TMP in sufficient purity.

US 2004/0254405 A1 discloses a process for recrystallization the distillation residue using organic solvents, for example acetone or methyl ethyl ketone, which requires a particular degree of observance for the crystallization temperature, the amount of solvent and the di-TMP content in the distillation residue. The use of a mixture of a suitable solvent and water for the isolation of di-TMP from the distillation residues of the trimethylolpropane preparation is described in DE 10 2008 038 021 A1 (counterpart to Publication 2012/0010435 of Rauchschwalbe et al.) An organic solvent phase and a viscous residue are initially obtained, the phases are separated and the organic solvent phase is extracted with water. The water phase is isolated and solvent residues present are removed. di-TMP is crystallized from the remaining water phase.

Various art relates to processes for obtaining di-TMP from secondary streams of the trimethylolpropane preparation. According to US 2013/0131391 A1 of Kreickmann et al., the high-boiling fractions and residues are dissolved in water and hydrogenated in the presence of an acidic compound to split formaldehyde-containing acetals. After removal of the solids, the hydrogenated material is then contacted both with basic and acidic ion exchangers. A trimethylolpropane-enriched product stream is distilled out of the aqueous eluate, and di-TMP remains as the distillation residue in sufficient quality.

Likewise WO2013/072008 A1 and WO2013/072006 A1 refer to the hydrogenation of the aqueous solution of the high-boiling fractions and residues in the presence of an acidic compound. After removal of the solid, low boilers are removed in a first distillation step. A trimethylolpropane-enriched product stream is obtained as a head fraction in a second distillation step and the bottom fraction is distilled in a third distillation step, in which di-TMP is obtained as the tops fraction and high boilers are removed as bottom fractions. According to WO 2013/072006 A1, a solid nickel catalyst is used in the hydrogenation step. Likewise, WO 2013/072007 A1 refers to a distillative process for obtaining di-TMP using a three- stage distillation process. In the first stage low boiling compounds and in the second stage intermediate boiling compounds are removed as tops fractions and the bottom fraction of the second distillation column is sent to a third distillation column in which di-TMP is obtained as a third distillation tops fraction and high boilers are removed as a bottom fraction.

Input stream for the distillation process according to WO 2013/072007 A1 is obtained, for e.g., in the preparation of trimethylolpropane as high-boiling fractions and residues with a certain content of di-TMP.

The art further refers to the deliberate or "on purpose" synthesis of di-trimethylolpropane from raw materials. According to EP 0 799 815 A1 (counterpart to U.S. Pat. No. 5,840,994 to Ninomiya et al.), trimethylolpropane is reacted directly with 2-ethylacrolein and formaldehyde in the presence of basic catalysts. After removing volatile components, purified ditrimethylopropane is obtained by recrystallization from water. According to WO92/05134 A1, already isolated trimethylolpropane is heated in the presence of an acidic compound, resulting in etherification to form di-trimethylolpropane.

JP2003335717 discloses the reaction of trimethylolpropane with the oxetane of trimethylolpropane (3-ethyl-3-hydroxymethyl-oxetane) in the presence of an acidic catalyst. So also, WO 01/14300 A1 discloses the ring opening reaction of trimethylolpropane oxetane with trimethylolpropane at elevated temperature in the presence of an acidic catalyst to provide ditrimethylolpropane. Neither reference provides guidance on an effective method to produce the oxetane of trimethylolpropane.

The oxetane of trimethylolpropane may be prepared by the reaction of trimethylol-propane with a carbamide, such as urea, in the presence of a catalyst such as zinc(II)acetate and potassium hydroxide according to U.S. Pat. No. 6,515,152 B1. See also GB 787,406 (Bayer). Other processes for preparing oxetanes per se using dialkyl carbonates or alkylene carbonates are discussed in Kokai Patent Application No. 10[1986]-7669 as well as Pattison, D. B., Cyclic Ethers Made by Pyrolysis of Carbonate Esters, J. Am. Chem. Soc., 1957, 79, vol 13, 3455-3456, Tan, Qiaohna et al. "Electrochemical Behaviors and Anion Recognition of Ferrocene Modified Hyperbranched Polyether." *Macromolecules*. (Washington, D.C., USA), 42(13), 4500-4510; 2009.

WIPO Publication No WO 2014/024717 (PCT/JP2013/070485) discloses a process for making polyhydric alcohol ethers in which the alcohol is dehydrated and condensed.

SUMMARY OF INVENTION

It has been found in accordance with the invention that di-TMP can be economically and efficiently produced from TMP and a dialkyl carbonate in a reaction medium using a process which does not require isolating intermediate product oxetane. In a first reaction stage, TMP is reacted with a dialkyl carbonate such as diethyl carbonate in the presence of a base catalyst to yield the oxetane of trimethylpropane. In a second reaction stage, TMP is reacted in situ in the reaction mixture with the oxetane of trimethylpropane in the presence of an acid catalyst to provide di-TMP:

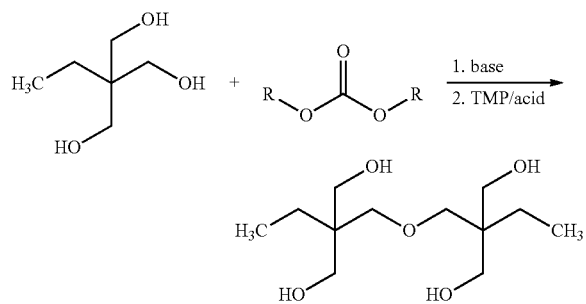

The process can be operated batchwise in a single reaction vessel or in a continuous sequential process such as in a pipe reactor, a recirculating loop reactor or a pair of CSTR reactors in series. A quasi-continuous process is carried out by operating two reaction zones batchwise in alternating fashion, if so desired.

Typical operation includes in the first reaction stage, trimethylolpropane reacts with di-alkyl carbonates $(RO)_2C=O$, in which the substituent R is independently equal or different and optionally an alkyl group having 1 to 5 carbon atoms, in the presence of a base at elevated temperature to provide the oxetane of trimethylolpropane. The first stage reaction is typically conducted at elevated temperature of 90° C. or so, optionally in the presence of a polar solvent, such as water or a lower aliphatic alcohol, in particular under reflux under ambient pressure. Then, the solvent, carbonate by-products and any excess of the di-alkylcarbonate may be distilled off. Alternatively, a Dean-Stark apparatus can be used to remove solvent, carbonate by-products and any excess of the di-alkylcarbonate prior to the second stage reaction.

The acid catalyzed reaction stage is preferably carried out at 120° C. or above.

A salient feature of the invention is to remove dialkyl carbonate derived byproducts during or immediately after the first stage of the process in order to achieve a good yield. Without intending to be bound by any particular theory, it is believed that removal of the carbonate byproducts drives the reaction to yield the desired intermediate oxetane. Alkyl carbonate byproducts of a dialkyl carbonate in the first stage include the corresponding alkanol and alkyl hydrogen carbonate. For example:

Diethyl carbonate=>ethanol and ethyl hydrogen carbonate; Dimethyl carbonate=>methanol and methyl hydrogen carbonate.

Preferably at least 75% by weight of the intermediate dialkyl carbonate byproducts formed are removed from the reaction mixture prior to the second stage of reaction and more preferably at least 90% by weight. Most preferably, over 95% by weight of the intermediate dialkyl carbonate byproducts formed are removed prior to the second stage of reaction.

In the second stage of the reaction, the oxetane of trimethylolpropane present in the reaction medium is reacted with additional trimethylpropane in the presence of an acid at elevated temperature. The acid compound is preferably provided as an aqueous acid such as methane sulfonic acid, sulfuric acid, hydrochloric acid or phosphoric acid, having an acid content of from 30 to 70% by weight or an acidic solid, such as a strong acid ion-exchange resin, such as a sulfonic acid ion exchange resin. Typically, the second stage reaction is carried out at a temperature of from 120° C. to 195° C. for a duration of from 15 minutes to 4 hours.

Generally, the molar ratio of TMP/dialkyl carbonate employed in the method of the invention is greater than 2.5 and less than 25.

In one embodiment, following the second stage reaction, the reaction mixture is allowed to cool and an alkaline substance is added to neutralize the acidic catalyst. The amount of the alkaline substance is up to 10% of the equivalent in excess calculated on the amount to neutralize the acidic catalyst. Suitable alkaline substances are alkali or alkaline earth metal hydroxides, carbonates, hydrogencarbonates or oxides, in particular alkali or alkaline earth metal carbonates, such as sodium carbonate or potassium carbonate are useful. They can be added in solid form or as an aqueous solution. If a solid strong acidic compound is used for the formation of di-TMP, the reaction mixture may be freed from the solid by filtration after the reaction is finished. The obtained mixture, preferably having a pH of from 7-9 is then subjected to a distillation under reduced pressure. Trimethylolpropane is collected as the first over-head fraction; and then, while increasing the bottom temperature di-TMP is collected as an over-head fraction in high purity.

Optionally, the first stage, the second stage or both stages may be conducted in the absence of solvents to reduce purification expense.

Further details and advantages will become apparent from the discussion which follows.

BRIEF DESCRIPTION OF DRAWING

The invention is described in detail below with reference to the drawings wherein.

DETAILED DESCRIPTION

Figure 1:
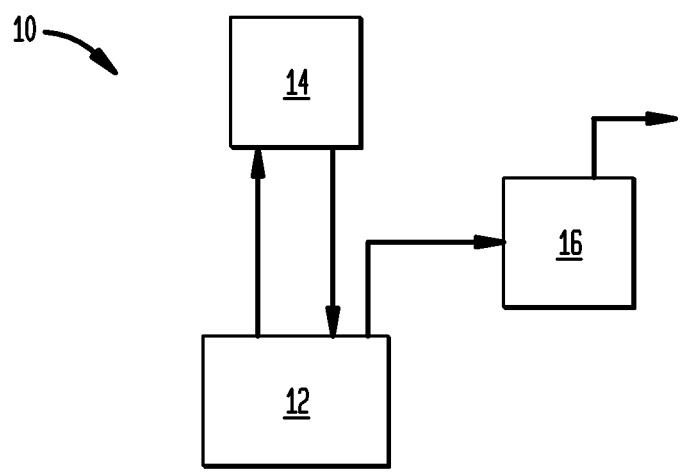
FIG. 1 is a schematic diagram illustrating an apparatus for making di-TMP in a single reaction vessel in accordance with the invention.

The invention is described in detail below in connection with the Figures for purposes of illustration, only. The invention is defined in the appended claims. Terminology used throughout the specification and claims herein are given their ordinary meanings as supplemented by the discussion below. For example, "duration" in a reaction vessel is synonymous with residence time in a reaction zone in a continuous reactor.

As used herein, "acid" refers to a protic acid, that is, an acid capable of donating a proton or a Lewis acid which may be a strong acid or a weak acid. Illustrative acids include mineral acids, sulfonic acids, carboxylic acids and the like as well as ion exchange resins incorporating acid moieties. Mineral acids or inorganic acids include hydrogen halides and their solutions such as: hydrofluoric acid (HF), hydrochloric acid (HCl), hydrobromic acid (HBr), hydroiodic acid (HI); Halogen oxoacids: hypochlorous acid (HClO), chlorous acid ($HClO_2$), chloric acid ($HClO_3$), perchloric acid ($HClO_4$), and corresponding compounds for bromine and iodine; sulfuric acid ($H_2SO_4$), fluorosulfuric acid ($HSO_3F$), nitric acid ($HNO_3$), phosphoric acid ($H_3PO_4$), fluoroantimonic acid ($HSbF_6$), fluoroboric acid ($HBF_4$), hexafluorophosphoric acid ($HPF_6$), chromic acid ($H_2CrO_4$); and boric acid ($H_3BO_3$). Sulfonic acids include: methanesulfonic acid (or mesylic acid, $CH_3SO_3H$), ethanesulfonic acid (or esylic acid, $CH_3CH_2SO_3H$), benzenesulfonic acid (or besylic acid, $C_6H_5SO_3H$), p-toluenesulfonic acid (or tosylic acid, $CH_3C_6H_4SO_3H$), trifluoromethanesulfonic acid (or triflic acid, $CF_3SO_3H$), and polystyrene sulfonic acid (sulfonated polystyrene, $[CH_2CH(C_6H_4)SO_3H]_n$). Carboxylic acids include: acetic acid ($CH_3COOH$), citric acid ($C_6H_8O_7$), formic acid (HCOOH), gluconic acid $HOCH_2—(CHOH)_4—COOH$, lactic acid ($CH_3—CHOH—COOH$), oxalic acid (HOOC—COOH), and tartaric acid (HOOC—CHOH—CHOH—COOH). Halogenation at alpha position increases acid strength, so that the following halogenated carboxylic acids are all stronger than acetic acid: fluoroacetic acid, trifluoroacetic acid, chloroacetic acid, dichloroacetic acid and trichloroacetic acid. A "strong" acid is any acid with a pKa of less than zero, preferably less than −1.74, whereas a weak acid has a higher pKa. Examples of weak acids are boric acid, boron trioxide.

The acid employed should be stable at the reaction temperature used in the process.

"Base" refers to a proton acceptor, including both weak and strong bases. A strong base is a base whose conjugate acid has a pKa of greater than 13, whereas the conjugate acid of a weak base has a pKa of less than 13. Strong bases thus include LiOH—lithium hydroxide; NaOH—sodium hydroxide; KOH—potassium hydroxide; RbOH—rubidium hydroxide; whereas weak bases include carbonates, bicarbonates, amines and ammonium hydroxides.

"Dialkyl carbonate" has its ordinary meaning and includes diethyl carbonate, dimethyl carbonate, ethylene carbonate and the like.

"Intermediate dialkyl carbonate byproducts" and like terminology refers to byproducts formed in the first stage of the inventive process, containing residue from the dialkyl carbonate. Such intermediate alkyl carbonate byproducts include alkanols and alkyl hydrogen carbonates corresponding to the dialkyl carbonate used as noted above. For purposes of calculating weight percent formed and weight percent removal of intermediate alkyl carbonate byproducts, intermediate alkyl carbonate byproducts can be considered to consist of alkanols and alkyl hydrogen carbonate(s) corresponding to the dialkyl carbonate(s) employed.

The molar ratio of TMP/dialkyl carbonate refers to the total moles of each reactant employed over the process of the invention.

A "stage" of a reaction system as used herein is a reaction zone with distinct characteristics as compared with other reaction zones of the system. The reaction zones can be physically separated as shown in FIG. 2 or a single vessel can be used to conduct different reactions which are temporally staged with respect to each other as shown in FIG. 1 and described in connection with Examples 1 and following.

Selectivity is determined (using gas chromatography analysis) by the mass percentage of di-TMP divided by the combined mass percentage of di-TMP and TMP containing oligomeric byproducts such as TMP trimers and the like.

Figure 2:
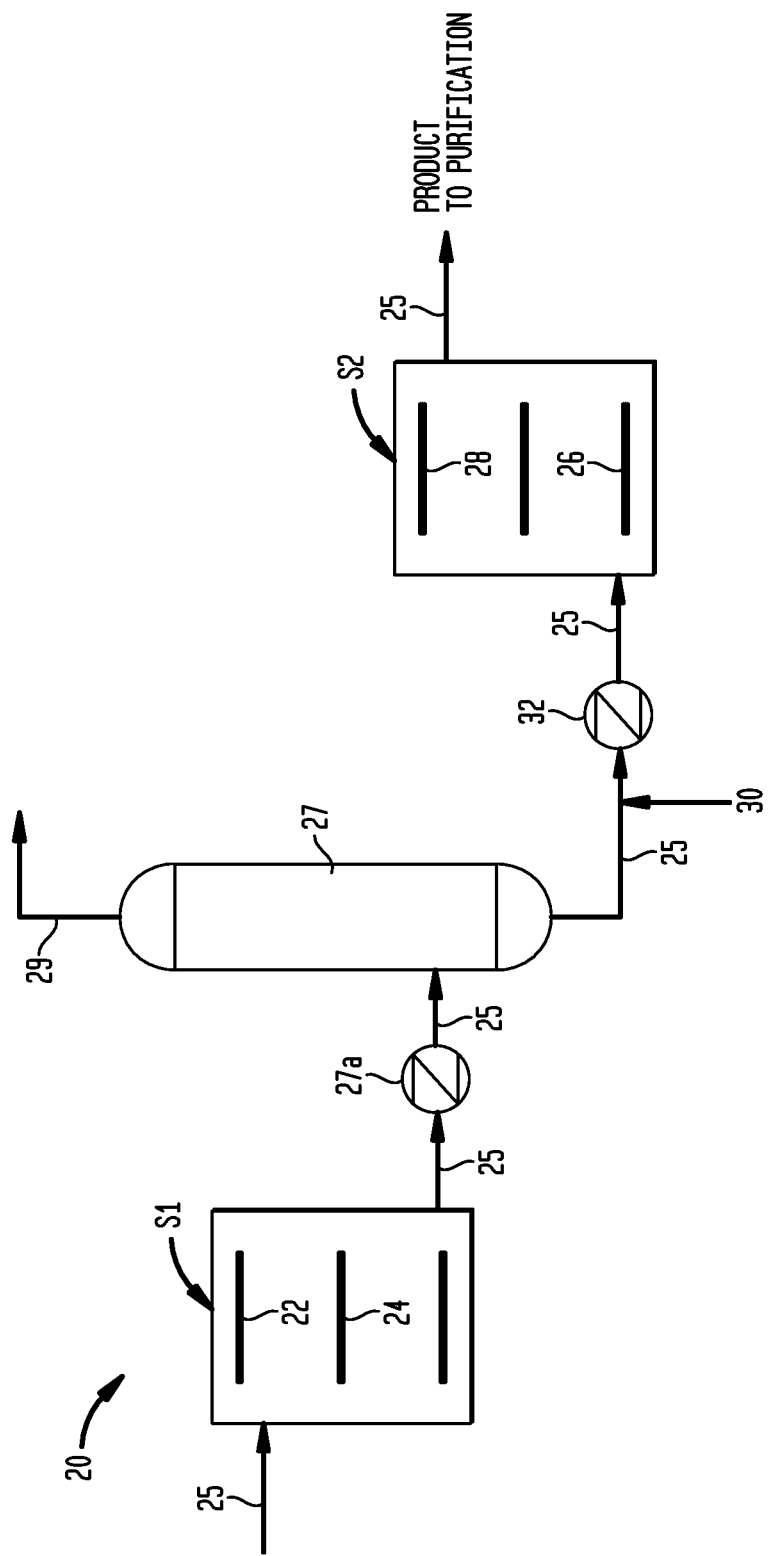
FIG. 2 is a schematic diagram illustrating an apparatus for making di-TMP in a two-stage reactor in a continuous process in accordance with the present invention.

"Successive" refers to a serial arrangement of reactor stages, for example, where a later reaction stage is downstream of an initial stage as is seen in FIG. 2.

Yields are determined by taking the actual yield (the mass of the final reaction mixture multiplied by the mass percent of di-TMP according to the gas chromatography scan) divided by the theoretical yield (the 100% yield as calculated by complete conversion of alkyl carbonate reactant into di-TMP product).

In accordance with the present invention, di-TMP can be produced in a single vessel as shown schematically in FIG. 1 wherein there is shown a reaction system 10 including a reaction vessel 12 fitted with a condenser 14 and a distillate recovery unit 16 with vacuum distillation capability. In operation, reactant dialkyl carbonate, TMP and a strong base catalyst and optionally solvent are changed to vessel 12 and reacted in a first reaction stage for a duration typically in the range of from 15 minutes to 4 hours to generate the oxetane of TMP. At the completion of the first reaction stage, distillate from the reaction mixture may be distilled overhead through unit 16 to remove by-product while the first stage of reaction proceeds to completion. Additional TMP is then added to vessel 12 along with strong acid which neutralizes the base and catalyzes the second stage of the reaction. The second stage of the reaction is carried out also for typical durations of from 15 minutes to 4 hours to produce di-TMP. Following neutralization of the acid catalyst, residual TMP and the di-TMP are recovered during vacuum distillation by way of unit 16.

The following examples illustrate more specifically operation of the apparatus generally of the class shown in FIG. 1.

Example 1

A mixture of TMP (26.8 g, 0.200 mol), diethyl carbonate (23.6 g, 0.200 mol), and a 45% aqueous solution of potassium hydroxide (0.222 g, 1.78 mmol) was refluxed for 1 hour (90° C.). The reaction mixture was then distilled at 85° C. overhead, to both complete the reaction and remove off the byproducts.

Molten TMP (188.65 g, 1.406 mol) (at a temperature less than 130° C.) was added to the remaining reaction mixture and stirred for 5 minutes. While stirring, a 50% aqueous solution of methanesulfonic acid (MSA) (1.380 g, 7.18 mmol) was added, and heated to reaction temperature (135° C.). The contents were heated and mixed (using a magnetic stirbar) for 1 hour at 135° C. The mixture was allowed to cool until boiling ceased, then 10% sodium carbonate (5 g) was added to the hot reaction mixture to neutralize the acid catalyst. Using a vacuum distillation apparatus (~1 mmHg), the TMP reactant was collected overhead, followed by the product di-TMP (56.0% yield, 86.9% selectivity to di-TMP).

Example 2

A mixture of TMP (26.80 g, 0.20 mol), diethyl carbonate (23.60 g, 0.20 mol), potassium hydroxide (0.10 g, 1.80 mmol), and 2 mL EtOH were combined in a flask equipped with a magnetic stirbar, thermometer, heating mantle, and reflux column. The mixture was heated to reflux at 85° C. for 60 minutes. Continuing heating, the byproducts and unreacted alkyl carbonate were then removed via distillation. Once complete, TMP (187.84 g, 1.40 mol) and a 50% aqueous solution of sulfuric acid (1.10 g, 5.62 mmol) were added to the flask, then the mixture was heated and stirred for 60 minutes at 130° C. The reaction mixture was then neutralized using a 10% aqueous solution of sodium carbonate to a pH of 7. Using distillation under reduced pressure (4 mmHg), the remaining TMP and product di-TMP were isolated (52.9% yield, 85.0% selectivity to di-TMP).

Example 3

A mixture of TMP (26.80 g, 0.20 mol), diethyl carbonate (23.60 g, 0.20 mol), potassium hydroxide (0.10 g, 1.80 mmol), and 2 mL EtOH were combined in a flask equipped with a magnetic stirbar, thermometer, heating mantle, and reflux column. The mixture was heated to reflux at 85° C. for 60 minutes. Continuing heating, the byproducts and unreacted alkyl carbonate were then removed via distillation. Once complete, TMP (14.09 g, 0.105 mol) and a 50% aqueous solution of sulfuric acid (0.76 g, 3.89 mmol) were added to the flask, then the mixture was heated and stirred for 90 minutes at 100° C. The reaction mixture was then neutralized using a 10% aqueous solution of sodium carbonate to a pH of 7. Using distillation under reduced pressure (4 mmHg), the remaining TMP and product di-TMP were isolated (59.0% selectivity to di-TMP).

Example 4

A mixture of TMP (26.80 g, 0.20 mol), diethyl carbonate (23.60 g, 0.20 mol), potassium hydroxide (0.10 g, 1.80 mmol), and 2 mL EtOH were combined in a flask equipped with a magnetic stirbar, thermometer, heating mantle, and reflux column. The mixture was heated to reflux at 85° C. for 60 minutes. Continuing heating, the byproducts and unreacted alkyl carbonate were then removed via distillation. Once complete, a 50% aqueous solution of sulfuric acid was added to neutralize the reaction mixture to a pH of 7. Molten TMP (187.84 g, 1.40 mol) was then added to the neutralized reaction mixture and stirred to solution. Activated strong acid resin (5.00 g, Amberlyst 15WET, a product of Dow Chemical Co.) was added to the flask, stirred vigorously, and then heated with stirring for 90 minutes at 130° C. Once complete, the resin was separated from the reaction mixture via filtration. Using distillation under reduced pressure (4 mmHg), the remaining TMP and product di-TMP were isolated from the reaction solution (26.5% yield, 92.0% selectivity to di-TMP).

Example 5

A mixture of TMP (22.81 g, 0.17 mol), diethyl carbonate (20.08 g, 0.17 mol), potassium hydroxide (0.09 g, 1.60 mmol), and 2 mL MeOH were combined in a flask equipped with a magnetic stirbar, thermometer, heating mantle, and reflux column. The mixture was heated to reflux at 85° C. for 60 minutes. Continuing heating, the byproducts and unreacted alkyl carbonate were then removed via distillation. Once complete, TMP (159.20 g, 1.19 mol) and a 50% aqueous solution of sulfuric acid (0.96 g, 4.91 mmol) were added to the flask, then the mixture was heated and stirred for 60 minutes at 135° C. The reaction mixture was then neutralized using a 10% aqueous solution of sodium carbonate to a pH of 7. Using distillation under reduced pressure (4 mmHg), the remaining TMP and product di-TMP were isolated (49.8% yield, 85.6% selectivity to di-TMP).

Example 6

A mixture of TMP (26.80 g, 0.20 mol), diethyl carbonate (23.60 g, 0.20 mol), and a 45% aqueous solution of potassium hydroxide (0.25 g, 2.00 mmol) were combined in a flask equipped with a magnetic stirbar, thermometer, heating mantle, and reflux column. The mixture was heated to reflux at 85° C. for 60 minutes. Continuing heating, the byproducts and unreacted alkyl carbonate were then removed via distillation. Once complete, TMP (187.84 g, 1.40 mol) and a 50% aqueous solution of methanesulfonic acid (0.65 g, 3.36 mmol) were added to the flask, then the mixture was heated and stirred for 60 minutes at 130° C. The reaction mixture was then neutralized using a 10% aqueous solution of sodium carbonate to a pH of 7. Using distillation under reduced pressure (4 mmHg), the remaining TMP and product di-TMP were isolated (38.9% yield, 83.4% selectivity to di-TMP).

Example 7

A mixture of TMP (28.17 g, 0.21 mol), diethyl carbonate (23.60 g, 0.20 mol), and a 45% aqueous solution of potassium hydroxide (0.22 g, 1.78 mmol) were combined in a flask equipped with a magnetic stirbar, thermometer, heating mantle, and reflux column. The mixture was heated to reflux at 85° C. for 60 minutes. Continuing heating, the byproducts and unreacted alkyl carbonate were then removed via distillation. Once complete, TMP (187.84 g, 1.40 mol) and a 50% aqueous solution of methanesulfonic acid (1.39 g, 7.23 mmol) were added to the flask, then the mixture was heated and stirred for 60 minutes at 130° C. The reaction mixture was then neutralized using a 10% aqueous solution of sodium carbonate to a pH of 7. Using distillation under reduced pressure (4 mmHg), the remaining TMP and product di-TMP were isolated.

Example 8

A mixture of TMP (26.8 g, 0.200 mol), diethyl carbonate (23.6 g, 0.200 mol), and a 45% aqueous solution of $Na_2CO_3$ (0.400 g, 1.70 mmol) was refluxed for 1 hour (90° C.). The reaction mixture was then distilled at 85° C. overhead, to both complete the reaction and remove off the byproducts. Molten TMP (188.65 g, 1.406 mol) (at a temperature less than 130° C.) was added to the remaining reaction mixture and stirred for 5 minutes. While stirring, a 50% aqueous solution of methanesulfonic acid (MSA) (1.380 g, 7.18 mmol) was added, and heated to reaction temperature (135° C.). The contents were heated and mixed (using a magnetic stirbar) for 1 hour at 135° C. The mixture was allowed to cool until boiling ceased, then 10% sodium carbonate (5 g) was added to the hot reaction mixture to neutralize the acid catalyst. Using a vacuum distillation apparatus (~1 mmHg), the TMP reactant was collected overhead, followed by the product di-TMP (27.7% yield, 98.0% selectivity to di-TMP).

Example 9

A mixture of TMP (26.8 g, 0.200 mol), diethyl carbonate (23.6 g, 0.200 mol), and a 45% aqueous solution of potassium hydroxide (0.222 g, 1.78 mmol) was refluxed for 1 hour (90° C.). The reaction mixture was then distilled at 85° C. overhead, to both complete the reaction and remove off the byproducts. Molten TMP (188.65 g, 1.406 mol) (at a temperature less than 130° C.) was added to the remaining reaction mixture and stirred for 5 minutes. While stirring, boric acid (2.32 g, 37.5 mmol) was added, and heated to reaction temperature (135° C.). The contents were heated and mixed (using a magnetic stirbar) for 1 hour at 135° C. The mixture was allowed to cool until boiling ceased, then 10% sodium carbonate (5 g) was added to the hot reaction mixture to neutralize the acid catalyst. Using a vacuum distillation apparatus (~1 mmHg), the TMP reactant was collected overhead, followed by the product di-TMP (1.5% yield, 6.6% selectivity to di-TMP).

Comparative Example A

This example demonstrates the need for carbonate byproduct removal following stage 1 reaction.

A mixture of TMP (13.40 g, 0.10 mol), diethyl carbonate (11.80 g, 0.10 mol), and a 45% aqueous solution of potassium hydroxide (0.11 g, 0.89 mmol) were combined in a flask equipped with a magnetic stirbar, thermometer, heating mantle, and reflux column. The mixture was heated to reflux at 85° C. for 60 minutes. Thereafter, TMP (94.33 g, 0.70 mol) and a 50% aqueous solution of methanesulfonic acid (0.69 g, 3.59 mmol) were added to the flask, then the mixture was heated and stirred for 120 minutes at 130° C. The reaction mixture was then neutralized using a 10% aqueous solution of sodium carbonate to a pH of 7. Using distillation under reduced pressure (4 mmHg), the remaining TMP and product di-TMP were isolated. Because the byproducts were not removed during the process, the yield was very low, about 3%.

Comparative Example B

To a flask equipped with a stirrer, thermometer, a Dean-Stark trap, and condenser, TMP (200 g, 1.49 mol), dimethyl carbonate (57.5 g, 0.64 mol), and potassium carbonate (0.2 g, 1.5 mmol) were mixed. The contents were heated and stirred at 90° C. and atmospheric pressure. Dimethyl carbonate (23 g, 0.255 mol) was fed into the flask over a period of 2 hrs and heated to 150° C. over 1.5 hrs. During this time, methanol and unreacted dimethyl carbonate were removed using the Dean-Stark trap. The reaction pressure is lowered to 1 mmHg over 1 hour with stirring and heating to facilitate the removal. After bringing the system to atmospheric pressure, boric acid (0.6 g, 0.010 mol) was charged into the flask, and the reaction temperature was raised to 200° C. and left to react for 6 hrs with heating and stirring.

Yield=26.0%. Selectivity to Di-TMP=80.4%

Comparative Example C

To a flask equipped with a stirrer, thermometer, fractionating column, and condenser, combine TMP (200 g), ethylene carbonate (85 g), and boron trioxide (0.03 g). The mixture is stirred and heated to 140-165° C. for 14 hours at a pressure of 0.045-0.0001 MPa (338-1 mmHg). During this time, distillate was removed from the system through the fractionating column and condenser. Then boron trioxide (2.15 g, 30.88 mmol) and potassium carbonate (2.15 g, 15 5 mmol) were added, and the reaction temperature was increased to 190° C. and maintained for 12 hours at atmospheric pressure.

Yield=13.6%. Selectivity to Di-TMP=26.4%

Results are summarized in Table 1 below.

TABLE 1

Selectivity and Yield

| Example | Dialkyl Carbonate | Base Catalyst | Acid Catalyst | TMP/Dialkyl Carbonate Ratio | Selectivity % | Yield % |
|---|---|---|---|---|---|---|
| 1 | Diethyl Carbonate | Potassium Hydroxide | Methanesulfonic Acid | 8 | 86.9 | 56 |
| 2 | Diethyl Carbonate | Potassium Hydroxide | Sulfuric Acid | 8 | 85.0 | 52.9 |
| 3 | Diethyl Carbonate | Potassium Hydroxide | Sulfuric Acid | 1.6 | 59.0 | — |
| 4 | Diethyl Carbonate | Potassium Hydroxide | Sulfonic Acid Resin | 8 | 92.0 | 26.5 |
| 5 | Diethyl Carbonate | Potassium Hydroxide | Sulfuric Acid | 8 | 86.6 | 49.8 |
| 6 | Diethyl Carbonate | Potassium Hydroxide | Methanesulfonic Acid | 8 | 83.4 | 38.9 |
| 7 | Diethyl Carbonate | Potassium Hydroxide | Methanesulfonic Acid | 8 | — | — |
| 8 | Diethyl carbonate | $Na_2CO_3$ | Methanesulfonic acid | 8 | 98.0% | 27.7% |
| 9 | Diethyl carbonate | KOH | Boric acid | 8 | 6.6% | 1.5% |
| A | Dimethyl Carbonate | Potassium Hydroxide | Methanesulfonic Acid | 8 | — | <3 |
| B | Dimethyl Carbonate | Potassium Carbonate | Boric Acid | 2.3 | 80.4 | 26.0 |
| C | Ethylene Carbonate | Potassium Carbonate | Boron Trioxide | 1.5 | 26.4 | 13.6 |

It will be appreciated from Table 1 that selectivities in the inventive process are substantially better when treatment with acid occurs above about 120° C. (Examples 1, 2 versus Example 3). Comparative Example A demonstrates the criticality of removing carbonate by-products during the process, while Example 9, Comparative Examples B, C demonstrate that weak acids and bases are much less effective in terms of selectivity and yield. Even when elevated temperatures and long reaction times are used, a weak base/weak acid processing protocol is much less effective than using a strong acid, for Example.

Moreover, it is seen that relatively high TMP/Dialkyl Carbonate ratios provide much better selectivities and yields, an unexpected result compared to prior art disclosures. Likewise, the fact that strong acids provide much better processing characteristics in terms of selectivities and yields especially at low temperatures is unexpected based on the prior art as is the fact that all other things being equal, a strong base provides better results than a weak base.

The di-TMP production method of the present invention may also be carried out in a continuous process using a multi-stage pipe reactor system as shown schematically in FIG. 2 wherein pipe reactor apparatus 20 has a first bank or stage S1 and a second stage or bank S2 of reaction tubes such as tubes 22, 24, 26, 28 and so forth. Each bank preferably has multiple tubes connected in series within each bank, each having 3-10 reaction tubes in series, if so desired.

A reaction medium stream 25 is fed to system 20 via a first reaction tube 22. Initially, the reaction stream includes TMP, a dialkyl carbonate and a strong base catalyst, optionally with reaction solvent. The mixture reacts in tube bank S1 while the reaction medium is advanced through tubes 22, 24 forming the oxetane of TMP.

Stream 25 is heated in a heat exchanger 27a as it exits tube bank S1 in order to raise the temperature at least 10, preferably 20-40° C. whereupon process stream 25 fed to an in-line separator 27 which may be a distillation column with or without packing or trays. Alternatively, separator 27 may be a flash vessel or evaporator. In separator 27, intermediate dialkyl byproducts derived from the dialkyl carbonate such as alkanols, alkyl hydrogen carbonate and the like are removed from stream 25 as a byproduct stream 29 in order to drive the reaction toward higher conversion of the reactants to the intermediate product oxetane. Unreacted dialkyl carbonate is also removed from the top of separator 27 in stream 29 which exits the reaction system. Stream 25 exits separator 27 and is advanced for further processing as indicated by the arrows in FIG. 2.

Additional TMP and a strong acid catalyst are added via a feed port 30 as the reaction medium stream 25 is fed forward to reaction tube bank S2 optionally through a heat exchanger 32 to adjust temperatures as may be necessary or expedient. For example, stream 25 may require cooling if a sharp temperature spike arises due to neutralization.

The reaction mixture further reacts in bank S2, wherein the oxetane in reaction medium stream 25 reacts with TMP to form di-TMP as medium 25 advances through tubes 26, 28. Thereafter, reaction medium stream 25 exits bank S2 of reaction system 20 and is further purified as described above in order to recover di-TMP from stream 25.

Instead of a pipe reactor with two reaction stages, the reaction can be carried out in two CSTR reactions connected in series with a configuration as is shown in FIG. 2, wherein section S1 is a first CSTR and section S2 is a second CSTR, the system otherwise operating in a similar manner.

Compendium of Preferred Embodiments of the Present Invention

It will be appreciated from the foregoing description that there is provided in accordance with a first embodiment of the present invention a method of making di-TMP comprising: (a) reacting TMP and a dialkyl carbonate in the presence of a base catalyst in a reaction medium to form an oxetane of TMP in the reaction medium; (b) removing intermediate dialkyl carbonate byproducts from the reaction medium and optionally removing any unreacted dialkyl carbonate present; (c) providing an acid catalyst to the reaction medium and reacting the oxetane formed in step (a) in situ with TMP to produce di-TMP; and (d) recovering di-TMP, with the further proviso that at least one of the following conditions are met: (i) said acid catalyst is a strong acid catalyst or (ii) said base catalyst is a strong base catalyst; or (iii) the molar ratio of TMP/dialkyl carbonate employed in the method is greater than 2.5.

Further features which may be combined into this first embodiment, Embodiment 1, are recited below in embodiments numbered 2 through 28:

Embodiment No. 2 is the method according to Embodiment 1, wherein said acid catalyst is a strong acid catalyst; Embodiment No. 3 is the method according to Embodiment 2, wherein said strong acid catalyst is selected form sulfonic acids, sulfuric acid, hydrochloric acid, phosphoric acid, nitric acid and strong acid ion-exchange resins; Embodiment No. 4 is the method according to any of the foregoing embodiments, wherein said base catalyst is a strong base catalyst; Embodiment No. 5 is the method according to Embodiment 4, wherein said strong base catalyst is selected from alkali-metal hydroxides and alkaline earth element hydroxides; Embodiment No. 6 is the method according to Embodiment 5, wherein said strong base catalyst is selected from potassium hydroxide, sodium hydroxide and lithium hydroxide; Embodiment No. 7 is the method according to Embodiment 1, wherein the molar ratio of TMP/dialkyl carbonate employed in the method is greater than 2.5 and less than 25; Embodiment No. 8 is the method according to Embodiment 7, wherein the molar ratio of TMP/dialkyl carbonate employed in the method is greater than 4; Embodiment No. 9 is the method according to Embodiment 7, wherein the molar ratio of TMP/dialkyl carbonate employed in the method is greater than 6.5; Embodiment No. 10 is the method according to Embodiment 1, wherein the molar ratio of TMP/dialkyl carbonate employed in the method is greater than 4 and less than 12.5; Embodiment No. 11 is the method according to Embodiment 1, wherein (i) said acid catalyst is a strong acid catalyst and (iii) the molar ratio of TMP/dialkyl carbonate employed in the method is greater than 2.5; Embodiment No. 12 is the method according to any of the foregoing embodiments, wherein the reaction of step (c) is carried out at a temperature of 120° C. or above; Embodiment No. 13 is the method according to any of the foregoing embodiments, wherein the reaction of step (c) is carried out at a temperature of from 120° C. to 195° C. for a duration of from 15 minutes to 4 hours; Embodiment No. 14 is the method according to any of the foregoing embodiments, wherein the reaction of step (c) is carried out at a temperature of from 120° C. to 150° C. for a duration of from 15 minutes to 4 hours; Embodiment No. 15 is the method according to any of the foregoing embodiments, wherein the reaction of step (a) is carried out at a temperature of from 75° C. to 195° C. for a duration of from 15 minutes to 4 hours; Embodiment No. 16 is the method according to Embodiment 1, wherein step (c) further comprises providing additional TMP to the reaction medium; Embodiment No. 17 is the method according to any of the foregoing embodiments, wherein the reaction mixture is neutralized with a base following the reaction to produce di-TMP and prior to di-TMP recovery from the reaction medium; Embodiment No. 18 is the method according to Embodiment 17, wherein the reaction medium is neutralized with a buffering base composition following the reaction to produce di-TMP and prior to di-TMP recovery from the reaction medium, the buffering base composition being provided in amounts effective to maintain the pH of the reaction medium between 6 and 9.5 prior to di-TMP recovery; Embodiment No. 19 is the method according to Embodiment 18, wherein the buffering base composition comprises an alkali metal carbonate; Embodiment No. 20 is the method according to any of the foregoing embodiments, wherein the dialkyl carbonate comprises a dialkyl carbonate with alkyl moieties having from 1 to 5 carbon atoms; Embodiment No. 21 is the method according to Embodiment 20, wherein the dialkyl carbonate is diethyl carbonate; Embodiment No. 22 is the method according to any of the foregoing embodiments, wherein TMP and the dialkyl carbonate are reacted with each other in step (a) in a molar ratio of TMP:dialkyl carbonate of from 3:1 to 1:3; Embodiment No. 23 is the method according to Embodiment 22, wherein TMP and the dialkyl carbonate are reacted with each other in step (a) in a molar ratio of TMP:dialkyl carbonate of from 1.25:1 to 1:1.25; Embodiment No. 24 is the method according to any of the foregoing embodiments, further comprising removing at least 75% by weight of intermediate dialkyl carbonate byproducts formed from the reaction medium prior to providing an acid catalyst thereto; Embodiment No. 25 is the method according to any of the foregoing embodiments, comprising removing at least 90% by weight of intermediate dialkyl carbonate byproducts formed from the reaction medium prior to providing an acid catalyst thereto; Embodiment No. 26 is the method according to any of the foregoing embodiments, further comprising removing more than 95% by weight of intermediate dialkyl carbonate byproducts formed from the reaction medium prior to providing an acid catalyst thereto; Embodiment No. 27 is the method according to any of the foregoing embodiments, wherein di-TMP is recovered by distilling the reaction medium; and Embodiment No. 28 is the method according to any of the foregoing embodiments, wherein the reactions of steps (a) and (c) are carried out in a single reaction vessel.

In another aspect of the invention there is provided still yet another embodiment, Embodiment 29 which is directed to a method of making di-TMP comprising: (a) feeding TMP, a dialkyl carbonate and a base catalyst to a first reaction zone to form a reaction medium in the first reaction zone; (b) reacting TMP and dialkyl carbonate in the reaction medium in the first reaction zone over a residence time of the reaction medium in the first reaction zone in the presence of said base catalyst, to form an oxetane of TMP in the reaction medium; (c) removing intermediate dialkyl carbonate byproducts from the reaction medium and optionally removing any unreacted dialkyl carbonate present; (d) feeding the reaction medium containing the oxetane of TMP, optionally additional TMP and an acid catalyst to a second reaction zone; (e) reacting the oxetane of TMP with TMP in the second reaction zone in the presence of said acid catalyst over a residence time in the second reaction zone to form di-TMP in the reaction medium; and (f) recovering di-TMP from the reaction medium.

Further features which may be combined into this Embodiment 29, are recited below in embodiments numbered 30 through 60:

Embodiment No. 30 is the method according to Embodiment 29, wherein the residence time of the reaction medium in the first reaction zone and the residence time of the reaction medium in the second reaction zone are each between 15 minutes and 4 hours; Embodiment No. 31 is the method according to Embodiment 30, wherein the residence time of the reaction medium in the first reaction zone and the residence time of the reaction medium in the second reaction zone are each between 30 minutes to 2 hours; Embodiment No. 32 is the method according to Embodiment 29, wherein temperature in the first reaction zone is maintained between 75° C. and 105° C.; Embodiment No. 33 is the method according to Embodiment 29, wherein temperature in the second reaction zone is maintained above 120° C.; Embodiment No. 34 is the method according to Embodiment 33, wherein temperature in the second reaction zone is maintained between 120° C. and 195° C.; Embodiment No. 35 is the method according to Embodiment 34, wherein temperature in the second reaction zone is maintained between 120° C. and 150° C. and the reaction with acid catalyst is carried out for a duration of from 15 minutes to 4 hours; Embodiment No. 36 is the method according to Embodiment 29, wherein TMP, the dialkyl carbonate and the base catalyst are continuously fed to the first reaction zone and the reaction medium is continuously removed from the first reaction zone; Embodiment No. 37 is the method according to Embodiment 36, wherein the process is carried out in a pipe reactor; Embodiment No. 38 is the method according to Embodiment 36, wherein the process is carried out in a pair of CSTR reactors arranged in series; Embodiment No. 39 is the method according to Embodiment 29, wherein additional TMP is added to the second reaction zone; Embodiment No. 40 is the method according to Embodiment 29, wherein at least one of the following conditions are met: (i) said acid catalyst is a strong acid catalyst or (ii) said base catalyst is a strong base catalyst; or (iii) the molar ratio of TMP/dialkyl carbonate employed in the method is greater than 2.5; Embodiment No. 41 is the method according to Embodiment 40 wherein (i) said acid catalyst is a strong acid catalyst and (iii) the molar ratio of TMP/dialkyl carbonate employed in the method is greater than 2.5; Embodiment No. 42 is the method according to any of any of Embodiments 29-41, wherein said acid catalyst is a strong acid catalyst; Embodiment No. 43 is the method according to Embodiment 42, wherein said strong acid catalyst is selected form sulfonic acids, sulfuric acid, hydrochloric acid, phosphoric acid, nitric acid and strong acid ion-exchange resins; Embodiment No. 44 is the method according to any of Embodiments 29-43, wherein said base catalyst is a strong base catalyst; Embodiment No. 45 is the method according to Embodiment 44, wherein said strong base catalyst is selected from alkali-metal hydroxides and alkaline earth element hydroxides; Embodiment No. 46 is the method according to Embodiment 45, wherein said strong base catalyst is selected from potassium hydroxide, sodium hydroxide and lithium hydroxide; Embodiment No. 47 is the method according to any of any of Embodiments 29-46, wherein the reaction mixture is neutralized with a base following the reaction to produce di-TMP and prior to di-TMP recovery from the reaction medium; Embodiment No. 48 is the method according to Embodiment 47, wherein the reaction medium is neutralized with a buffering base composition following the reaction to produce di-TMP and prior to di-TMP recovery from the reaction medium; the buffering base composition being provided in amounts effective to maintain the pH of the reaction medium between 6 and 9.5 prior to di-TMP recovery; Embodiment No. 49 is the method according to Embodiment 48, wherein the buffering base composition comprises an alkali metal carbonate; Embodiment No. 50 is the method according to any of Embodiments 29-49, wherein the dialkyl carbonate comprises a dialkyl carbonate with alkyl moieties having from 1 to 5 carbon atoms; Embodiment No. 51 is the method according to Embodiment 50, wherein the dialkyl carbonate is diethyl carbonate; Embodiment No. 52 is the method according to Embodiment 29, wherein the molar ratio of TMP/dialkyl carbonate employed in the method is greater than 2.5 and less than 25; Embodiment No. 53 is the method according to Embodiment 29, wherein the molar ratio of TMP/dialkyl carbonate employed in the method is greater than 4; Embodiment No. 54 is the method according to Embodiment 29, wherein the molar ratio of TMP/dialkyl carbonate employed in the method is greater than 6.5; Embodiment No. 55 is the method according to Embodiment 29, wherein the molar ratio of TMP/dialkyl carbonate employed in the method is greater than 4 and less than 12.5; Embodiment No. 56 is the method according to any of Embodiments 29-55, comprising removing at least 75% by weight of intermediate dialkyl carbonate byproducts formed from the reaction medium prior to providing an acid catalyst thereto; Embodiment No. 57 is the method according to any of Embodiments 29-56, comprising removing at least 90% by weight of intermediate dialkyl carbonate byproducts formed from the reaction medium prior to providing an acid catalyst thereto; Embodiment No. 58 is the method according to any of Embodiments 29-57, comprising removing more than 95% by weight of intermediate dialkyl carbonate byproducts formed from the reaction medium prior to providing an acid catalyst thereto; Embodiment No. 59 is the method according to any of Embodiments 29-58, wherein the reaction of step (b) is carried out at a temperature of from 75° C. to 105° C. for a duration of from 15 minutes to 4 hours; and Embodiment No. 60 is the method according to any of Embodiments 29-59, wherein di-TMP is recovered by distilling the reaction medium.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention, the disclosures of which are all incorporated herein by reference, further description is deemed unnecessary. In addition, it should be understood from the foregoing discussion that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of making di-TMP comprising:
   (a) reacting TMP and a dialkyl carbonate in the presence of a base catalyst in a reaction medium to form an oxetane of TMP in the reaction medium;
   (b) removing intermediate dialkyl carbonate derived byproducts from the reaction medium and optionally removing any unreacted dialkyl carbonate present;
   (c) providing an acid catalyst and additional TMP to the reaction medium and reacting the oxetane formed in step (a) in situ with TMP to produce di-TMP; and
   (d) recovering di-TMP,
   with the further proviso that at least one of the following conditions are met: (i) said acid catalyst is a strong acid catalyst or (ii) said base catalyst is a strong base catalyst; or (iii) the molar ratio of TMP/dialkyl carbonate employed in the method is greater than 2.5.

2. The method according to claim 1, wherein said acid catalyst is a strong acid catalyst.

3. The method according to claim 2, wherein said strong acid catalyst is selected form sulfonic acids, sulfuric acid, hydrochloric acid, phosphoric acid, nitric acid and strong acid ion-exchange resins.

4. The method according to any of the foregoing claims, wherein said base catalyst is a strong base catalyst.

5. The method according to claim 2, wherein said base catalyst is a strong base catalyst selected from alkali-metal hydroxides and alkaline earth element hydroxides.

6. The method according to claim 5, wherein said strong base catalyst is selected from potassium hydroxide, sodium hydroxide and lithium hydroxide.

7. The method according to claim 1, wherein the molar ratio of TMP/dialkyl carbonate employed in the method is greater than 2.5 and less than 25.

8. The method according to claim 7, wherein the molar ratio of TMP/dialkyl carbonate employed in the method is greater than 6.5.

9. The method according to claim 1, wherein (i) said acid catalyst is a strong acid catalyst and (iii) the molar ratio of TMP/dialkyl carbonate employed in the method is greater than 2.5.

10. The method according to claim 1, wherein the reaction of step (c) is carried out at a temperature of from 120° C. to 195° C. for a duration of from 15 minutes to 4 hours.

11. The method according to claim 1, wherein the reaction of step (a) is carried out at a temperature of from 75° C. to 195° C. for a duration of from 15 minutes to 4 hours.

12. The method according to claim 1, wherein the dialkyl carbonate comprises a dialkyl carbonate with alkyl moieties having from 1 to 5 carbon atoms.

13. The method according to claim 12, wherein the dialkyl carbonate is diethyl carbonate.

14. The method according to claim 1, further comprising removing at least 75% by weight of intermediate dialkyl carbonate derived byproducts formed from the reaction medium prior to providing an acid catalyst thereto.

15. The method according to claim 1, comprising removing at least 90% by weight of intermediate dialkyl carbonate derived byproducts formed from the reaction medium prior to providing an acid catalyst thereto.

16. A method of making di-TMP comprising:
   (a) feeding TMP, a dialkyl carbonate and a base catalyst to a first reaction zone to form a reaction medium in the first reaction zone;
   (b) reacting TMP and dialkyl carbonate in the reaction medium in the first reaction zone over a residence time of the reaction medium in the first reaction zone in the presence of said base catalyst, to form an oxetane of TMP in the reaction medium;
   (c) removing intermediate dialkyl carbonate derived byproducts from the reaction medium and optionally removing any unreacted dialkyl carbonate present;
   (d) feeding the reaction medium containing the oxetane of TMP, optionally additional TMP and an acid catalyst to a second reaction zone;
   (e) reacting the oxetane of TMP with TMP in the second reaction zone in the presence of said acid catalyst over a residence time in the second reaction zone to form di-TMP in the reaction medium; and
   (f) recovering di-TMP from the reaction medium.

17. The method according to claim 16, wherein the residence time of the reaction medium in the first reaction zone and the residence time of the reaction medium in the second reaction zone are each between 15 minutes and 4 hours.

18. The method according to claim 16, wherein the process is carried out in a pipe reactor.

19. The method according to claim 16, wherein the process is carried out in a pair of CSTR reactors arranged in series.

20. A method of making di-TMP comprising:
   (a) reacting TMP and a dialkyl carbonate in the presence of a strong base catalyst in a reaction medium to form an oxetane of TMP in the reaction medium, wherein TMP and the dialkyl carbonate are reacted with each other in a molar ratio of TMP:dialkyl carbonate of from 3:1 to 1:3;
   (b) removing intermediate dialkyl carbonate derived byproducts from the reaction medium and optionally removing any unreacted dialkyl carbonate present;
   (c) providing additional TMP and an acid catalyst to the reaction medium and reacting the oxetane formed in step (a) in situ with TMP to produce di-TMP, wherein the amount of additional TMP added is such that the molar ratio of TMP/dialkyl carbonate employed in the method is greater than 4; and
   (d) recovering di-TMP.

21. The method according to claim 20, wherein TMP and the dialkyl carbonate are reacted with each other in step (a) in a molar ratio of TMP:dialkyl carbonate of from 1.25:1 to 1:1.25.

22. The method according to claim 20, wherein the molar ratio of TMP/dialkyl carbonate employed in the method is greater than 6.5.

23. The method according to claim 20, wherein the molar ratio of TMP/dialkyl carbonate employed in the method is greater than 4 and less than 12.5.

* * * * *